(12) United States Patent
Burke (10) Patent No.: US 10,667,741 B2
(45) Date of Patent: Jun. 2, 2020

(54) DEVICE AND METHOD FOR DETECTING FLATUS

(71) Applicant: Bradley Burke, Metamora, MI (US)

(72) Inventor: Bradley Burke, Metamora, MI (US)

(73) Assignee: 2innovate LLC, Metamora, MI (US)

( * ) Notice: Subject to any disclaimer, the term of this patent is extended or adjusted under 35 U.S.C. 154(b) by 800 days.

(21) Appl. No.: 15/010,123

(22) Filed: Jan. 29, 2016

(65) Prior Publication Data

US 2017/0215787 A1 Aug. 3, 2017

(51) Int. Cl.
*A61B 5/00* (2006.01)
*A61B 5/07* (2006.01)

(52) U.S. Cl.
CPC .......... *A61B 5/4255* (2013.01); *A61B 5/0002* (2013.01); *A61B 5/073* (2013.01); *A61B 5/4848* (2013.01); *A61B 5/6804* (2013.01); *A61B 5/6808* (2013.01); *A61B 5/6861* (2013.01); *A61B 5/74* (2013.01)

(58) Field of Classification Search
CPC .............. A23V 2200/32; A61B 5/4255; A61B 5/6804; A61B 2010/0083; A61B 5/6808
USPC .......... 600/309, 587, 593; 604/361, 335, 333
See application file for complete search history.

(56) References Cited

U.S. PATENT DOCUMENTS

| | | | |
|---|---|---|---|
| 4,376,127 A * | 3/1983 | Lunde | A23L 11/33 426/46 |
| 4,728,499 A | 3/1988 | Fehder | |
| 5,166,075 A | 11/1992 | Fehder | |
| 6,576,474 B2 | 6/2003 | Wallach | |
| 6,589,761 B1 | 7/2003 | Freadman et al. | |
| 7,578,971 B2 | 8/2009 | Ratner et al. | |
| 7,737,322 B2 | 6/2010 | Ales, III et al. | |
| 7,913,332 B1 * | 3/2011 | Barnhart | A47C 21/044 5/423 |
| 8,177,809 B2 | 5/2012 | Marvani et al. | |

(Continued)

FOREIGN PATENT DOCUMENTS

GB 2512575 10/2014

OTHER PUBLICATIONS

Calloway, D.H., "Gas in the Alimentary Canal," in Handbook of Physiology (ed. C. F. Code), sec. 6, vol. 5, ch. 137, pp. 2839, 2486-2487 Washington D.C.: American Physiological Society, 1968.

(Continued)

*Primary Examiner* — May A Abouelela
(74) *Attorney, Agent, or Firm* — Brooks Kushman P.C.

(57) ABSTRACT

A device and methods for using a device, for determining a passing of flatus is described. The device comprises a sleeve comprising a first porous gas-permeable surface, a second surface attached to the first porous gas-permeable surface defining a pocket within the sleeve, and a flatus detector inserted within the pocket of the sleeve and positioned between the first porous gas-permeable surface and the second surface. The flatus detector may be a dry-surface carbon dioxide detector that irreversibly changes colour upon contact with increased concentrations of $CO_2$ gas, a chemiresistor, or a near field communication tag. The chemiresistor or near field communication tag may be modified for detecting target gases. The device may be a patch that is affixed to a patient or attached to a garment that is worn by the patient, or a capsule, with a detector disposed therein.

28 Claims, 5 Drawing Sheets

(56) References Cited

U.S. PATENT DOCUMENTS

| | | | |
|---|---|---|---|
| 9,119,748 B2 | 9/2015 | Abraham et al. | |
| 9,931,252 B2* | 4/2018 | Carney | A61F 13/42 |
| 2002/0032386 A1* | 3/2002 | Sackner | A61B 5/0205 |
| | | | 600/536 |
| 2003/0097107 A1* | 5/2003 | Sprengard-Eichel | A61F 13/15203 |
| | | | 604/378 |
| 2004/0220538 A1* | 11/2004 | Panopoulos | A61F 13/42 |
| | | | 604/361 |
| 2006/0216828 A1 | 9/2006 | Ratner et al. | |
| 2007/0191794 A1* | 8/2007 | Cline | A61F 5/445 |
| | | | 604/335 |
| 2011/0152806 A1* | 6/2011 | Zhou | A61F 13/42 |
| | | | 604/361 |
| 2012/0004181 A1 | 1/2012 | Medina-Kauwe | |
| 2012/0310190 A1* | 12/2012 | LaVon | A61F 13/42 |
| | | | 604/361 |
| 2012/0310191 A1* | 12/2012 | LaVon | A61F 13/42 |
| | | | 604/361 |
| 2012/0330224 A1* | 12/2012 | Mailova | A61M 13/003 |
| | | | 604/24 |
| 2013/0095459 A1* | 4/2013 | Tran | A61B 5/6816 |
| | | | 434/247 |
| 2013/0096399 A1 | 4/2013 | Scalici et al. | |
| 2013/0110063 A1* | 5/2013 | Abraham | A61F 13/42 |
| | | | 604/361 |
| 2013/0110064 A1* | 5/2013 | Richardson | A61F 13/49 |
| | | | 604/361 |
| 2013/0344045 A1* | 12/2013 | Faure | A23L 33/21 |
| | | | 424/93.45 |
| 2014/0011286 A1* | 1/2014 | Potyrailo | G01N 33/0031 |
| | | | 436/149 |
| 2014/0135722 A1* | 5/2014 | Dougherty, Jr. | A61F 13/42 |
| | | | 604/361 |
| 2014/0200538 A1* | 7/2014 | Euliano | A61F 13/42 |
| | | | 604/361 |
| 2014/0257231 A1* | 9/2014 | Wang | A61F 13/514 |
| | | | 604/394 |
| 2015/0116093 A1 | 4/2015 | Swager et al. | |
| 2015/0257942 A1* | 9/2015 | Kim | A61F 13/42 |
| | | | 604/361 |
| 2017/0156947 A1* | 6/2017 | Esquerra | A61F 13/15203 |
| 2018/0184976 A1* | 7/2018 | Kuniavsky | A61B 5/6808 |

OTHER PUBLICATIONS

Isaksson, K. et al., "Small Bowel Obstruction: Early Parameters Predicting the Need for Surgical Intervention," European Journal of Trauma and Emergency Surgery, 37(2), pp. 155-159, 2011.

Klappenbach, R.F., et al., "Early Oral Feeding Versus Traditional Postoperative Care After Abdominal Emergency Surgery: A Randomized Controlled Trial," World J. Surg., 37, pp. 2293-2299, 2013.

Manichanh, C., et al., "Anal Gas Evacuation and Colonic Microbiota in Patients With Flatulence: Effect of Diet," Gut, pp. 1-8, 2013.

Pragatheeswarane, M., et al., "Early Oral Feeding vs. Traditional Feeding in Patients Undergoing Elective Open Bowel Surgery—a Randomized Controlled Trial," J. Gastrointest Surg, 18, pp. 1017-1023, 2014.

Suarez, F.L., et al., "Identification of Gases Responsible for the Odour of Human Flatus and Evaluation of a Device Purported to Reduce This Odour," Gut, 43 pp. 100-104, 1998.

Terai, T., et al., "Detection of Flatus Using a Portable Hydrogen Gas Analyzer," J Clin Anesth., 15(7), pp. 570-571, 2003.

Tomlin et al., "Investigation of Normal Flatus Production in Healthy Volunteers," Gut, 32, pp. 665-669, 1991.

Willcutts, K., "Pre-op NPO and Traditional Post-Op Diet Advancement: Time to Move on," Nutrition issues in gastroenterology, Practical Gastroenterology, 12, pp. 16-27, 2010.

Yukioka, H, et al., "Recovery of Bowel Motility After Surgery, Detection of Time of First Flatus From Carbon Dioxide Concentration and Patient Estimate After Nalbuphine and Placebo," Br J Anaesth., 59(5), pp. 581-584, 1987.

ISR & Written Opinion for PCT Application No. PCT/CA2017/050100 dated May 10, 2017.

* cited by examiner

DEVICE AND METHOD FOR DETECTING FLATUS

TECHNICAL FIELD

The present disclosure relates to a device and method for detecting flatus.

BACKGROUND

The passing of "first flatus" is a common medical indicator that helps surgeons decide when to begin feeding patients who have undergone abdominal procedures. Patients with a history of prior intestinal resection, perforation or abscess with sepsis, short gut, or intestinal hypomotility disorders, are typically not eligible to resume feeding until the passing of "first flatus" for safety reasons. Additionally, patients that have undergone complicated non-elective (emergency) abdominal procedures, suffer from cognitive impairments, or are at high risk of developing aspiration pneumonia, are also not eligible to resume feeding until the passing of "first flatus". For patients with prior intestinal resection or those that have undergone abdominal procedures (and are not trustworthy historians e.g. young children, demented patients, and the like), determining if a patient has passed "first flatus" is very important. However, it may be difficult for a clinician to determine when "first flatus" has passed and when to initiate feeding.

Feeding some patients too early can result in life-threatening complications leading to death, or dramatically lengthened hospital stays. Waiting too long to feed some patients can also increase the length of a hospital stay. Through determination of whether and when a patient has passed "first flatus", a more efficient and efficacious patient recovery plan may be implemented.

Bowel motility can be determined by placing a stethoscope on a patient's abdomen and listening for indications of motility. However, such a determination is not a reliable means of determining whether or not there is normal bowel motility, or whether an obstruction in the intestines is present.

The percent of carbon dioxide in flatus is about 5-80% and usually about 10-30% (Calloway, D. H. (1968). Gas in the alimentary canal; in Handbook of Physiology (ed. C. F. Code), section 6, volume 5, chapter 137, page 2839, Washington D.C.: American Physiological Society). Flatus typically contains higher concentrations of carbon dioxide than what is in the atmosphere, and almost always contains hydrogen gas that is in significantly higher concentrations than what is in the atmosphere. As such, when carbon dioxide is detected by the carbon dioxide detector at concentrations significantly higher than that of atmospheric levels, then the passing of flatus is deemed to have occurred. The passing of flatus has been be determined using a carbon dioxide detector (Yukioka H. et al., *Br J Anaesth*, 1987, 59(5): 581-584). However, the particular carbon dioxide detector disclosed by Yukioka et al. is not a practical inexpensive device capable of detecting flatus on a routine basis in a hospital, nursing home, or community setting.

SUMMARY

The present disclosure relates to a device adapted for detecting a passing of flatus.

It is an object of the present disclosure to provide a device for detecting a passing of flatus in a patient or a subject. The device may be used to detect the passing of flatus in a patient or subject who is not a reliable historian, for example, a patient suffering from dementia or delirium, a young child, a paralyzed or sedated patient, and the like. The device may be used to assist health care professionals to determine whether a patient or subject has recovered adequate bowel motility.

The present disclosure provides a device for detecting a passing of flatus by a patient. The device comprises a sleeve having a first porous gas-permeable surface and a second surface attached to the first porous gas-permeable surface defining a pocket within the sleeve. A flatus detector is inserted within the pocket of the sleeve and positioned between the first porous gas-permeable surface and the second surface. The porous gas-permeable surface device may be a hypoallergenic mesh.

The present disclosure also describes the device as defined above, where the sleeve further comprises a fastener attached to the sleeve. The fastener may be used to attach the sleeve to a garment using any suitable fastening mechanism, for example, one or more clips, one or more snaps, one or more patches or strips of hook and loop fasteners, a zipper, or an adhesive applied to a portion or all of the first porous gas-permeable surface, the adhesive for attaching the sleeve to a patient.

The flatus detector used in the device as described above may be a dry-surface flatus detector comprising an indicating solution that is dried onto, embedded into, or applied onto a carrier substrate, the indicating solution undergoing an irreversible colour change in the presence of increased concentrations of a target gas, for example, increased carbon dioxide gas, methane gas, hydrogen gas, or a combination of carbon dioxide gas, methane gas, and hydrogen gas. The dried indicating solution may be pH-sensitive, for example the dried pH-sensitive indicating solution may be Bordeaux. The flatus detector may be a chemiresistor or a near field communication tag. If the flatus detector is a near field communication (NFC) tag, then the NFC may include chemi-responsive nano-materials integrated into the circuitry of the near field communication tag for the detection of flatus.

The present disclosure also provides a device as defined above, wherein the device is a garment and the sleeve is attached to an inner lining of the garment via the fastener. For example, the garment may be a diaper.

Also described is a device as defined above, wherein the device is a diaper, and the sleeve comprising the flatus detector is incorporated into the diaper so that at least a portion of an inner lining of the diaper is the first porous gas-permeable surface, and the second surface of the sleeve is located between the inner lining and an outer lining of the diaper, or the second surface of the sleeve is a portion of the outer lining of the diaper. Alternatively, the second surface may be a portion of the outer lining of the diaper, and the second surface may comprise a transparent window. The flatus detector may be placed between the transparent window of the second surface and at least the portion of the inner lining of the diaper that is the first porous gas-permeable surface. With this arrangement, when the flatus detector is inserted into the sleeve, the flatus detector is visible through the transparent window.

The present disclosure further describes a device, wherein the device is a diaper as described above, and the second surface is a portion of the outer lining. The second surface may further comprise a transparent window, the flatus detector may be inserted between the transparent window of the second surface and at least the portion of the inner lining of the diaper that is the first porous gas-permeable surface. With this arrangement, the flatus detector is visible through the transparent window.

The present disclosure also provides the device, wherein the device is a diaper as defined above, and the portion of the inner lining of the diaper that is the first porous gas-permeable surface is further coupled to a gas-permeable hydrophobic layer.

The present disclosure also provides a method of detecting a passing of flatus by a patient comprising, (a) positioning the device as described above over an anus of the patient, such that the flatus detector covers the anus; and (b) monitoring the device to determine if the flatus detector indicates levels of a targeted gas that is greater than atmospheric levels of the targeted gas.

Also provided is device for detecting a passing of flatus by a patient comprising, a capsule comprising a perforated shell, the shell covered with a discontinuous biocompatible coating comprising perforations, or a continuous gas-permeable biocompatible coating, and a flatus detector inserted within the shell.

A method of detecting a passing of flatus by a patient using the device comprising a capsule as described above, comprises:

(a) positioning the capsule within a bowel or intestinal tract of the patient; and (b) monitoring the device to determine if the flatus detector indicates changes in the levels of a gas that is greater or less than a baseline level of the gas within the bowel or intestinal tract. The change in the level or amount of gas that may be detected may be a rapid change, for example a change in the level or amount of gas taking place within about 1-120 seconds, or any amount therebetween.

The device as described above may be used for detecting flatus in a patient or a subject, especially a patient or subject who is not reliable historian. Patients or subjects who are not reliable historians include those who suffer from dementia or delirium, young children, paralyzed or sedated patients, and the like. The device as described above comprising the flatus detector may be used to assist health care professionals to determine whether a patient or subject has recovered adequate bowel motility.

This summary does not necessarily describe the entire scope of all aspects of the disclosure. Other aspects, features and advantages will be apparent to those of ordinary skill in the art upon review of the following description of specific embodiments.

BRIEF DESCRIPTION OF THE DRAWINGS

These and other features of the invention will become more apparent from the following description in which reference is made to the appended drawings wherein:

FIGS. 1A and 1B show a sleeve of the device in accordance with an embodiment of the present invention.

FIGS. 3A and 3B show a sleeve of the device in accordance with an embodiment of the present invention.

FIGS. 4a and 4B show an alternate device in accordance with an embodiment of the present invention.

DETAILED DESCRIPTION

The present disclosure relates to a device and method for detecting a passing of flatus. The device may be termed "a flatus detector".

Directional terms such as "top," "bottom," "upwards," "downwards," "vertically," and "laterally" are used in the following description for the purpose of providing relative reference only, and are not intended to suggest any limitations on how any article is to be positioned during use, or to be mounted in an assembly or relative to an environment. The use of the word "a" or "an" when used herein in conjunction with the term "comprising" may mean "one," but it is also consistent with the meaning of "one or more," "at least one" and "one or more than one." Any element expressed in the singular form also encompasses its plural form. Any element expressed in the plural form also encompasses its singular form. The term "plurality" as used herein means more than one, for example, two or more, three or more, four or more, and the like.

As used herein, the term "about" refers to an approximately +/−10% variation from a given value. It is to be understood that such a variation is always included in any given value provided herein, whether or not it is specifically referred to.

As used herein, the terms "comprising," "having," "including," and "containing," and grammatical variations thereof, are inclusive or open-ended and do not exclude additional, unrecited elements and/or method steps. The term "consisting essentially of" when used herein in connection with a composition, use or method, denotes that additional elements, method steps or both additional elements and method steps may be present, but that these additions do not materially affect the manner in which the recited composition, method or use functions. The term "consisting of" when used herein in connection with a composition, use or method, excludes the presence of additional elements and/or method steps.

The composition of flatus, or intestinal gas, includes predominantly is the a byproduct of bacterial fermentation in the gastrointestinal tract. The majority of the volume of flatus is comprised of oxygen, nitrogen, carbon dioxide, hydrogen and methane gasses, and hydrogen; carbon dioxide and methane are usually the predominate gasses on a per volume basis. Additional compounds present in flatus include benzopyrrole volatiles indole and skatole, ammonia, short chain fatty acids and volatile sulfur compounds, such as hydrogen sulfide ($H_2S$), methyl mercaptan, methanethiol, dimethyl sulfide (DMS), dimethyl disulfide (DMDS) and dimethyl trisulfide (DMTS). Collectively these gases and potentially others may be referred to herein as flatus, a target gas, as compounds that comprise flatus, or as components of flatus.

Any of the compounds that comprise flatus, for example, oxygen, nitrogen, carbon dioxide, hydrogen, methane, volatile sulfur compounds, ammonia, indole, skatole, and short chain fatty acids, either alone, or in combination, may be detected using the flatus detector as described herein. Similarly, any of the compounds that comprise flatus, for example, oxygen, nitrogen, carbon dioxide, hydrogen, methane, volatile sulfur compounds, ammonia, indole, skatole, and short chain fatty acids, either alone, or in combination, may be used to determine a passing of flatus using the methods as described herein.

Flatus Detector

Figure 1A:
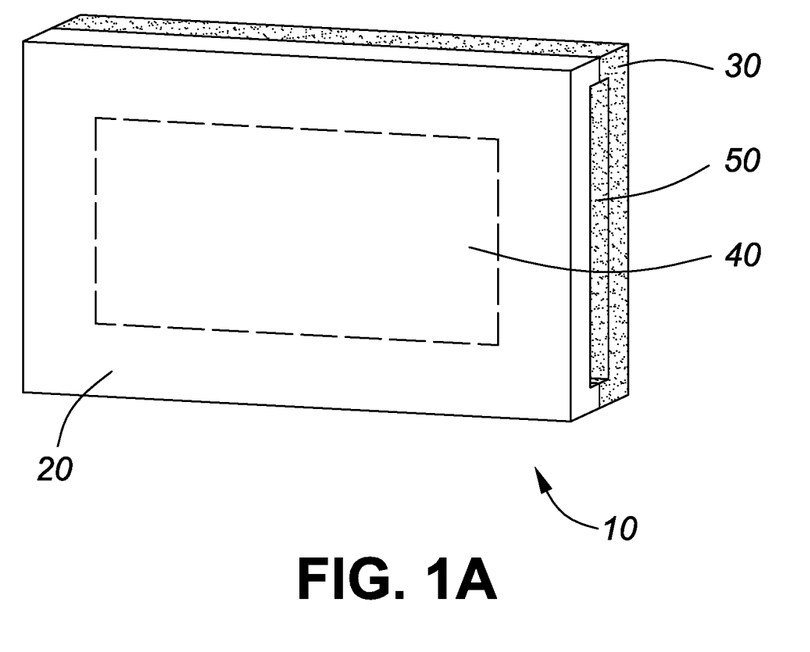
FIG. 1A shows a side view of the sleeve with a first porous gas-permeable surface 20, a second surface 30, a pocket or sleeve opening 50, and a flatus detector 40 (outlined in a dashed line) inserted within the sleeve.
Figure 1B:
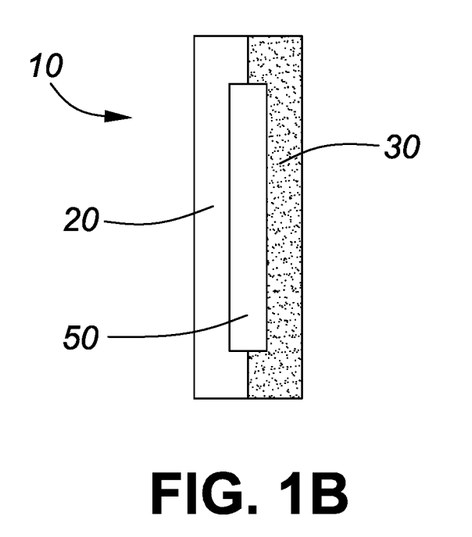
FIG. 1B shows a front end view of the sleeve with the first porous gas-permeable surface 20, the second surface 30, and the pocket or sleeve opening 50.
Figure 2:
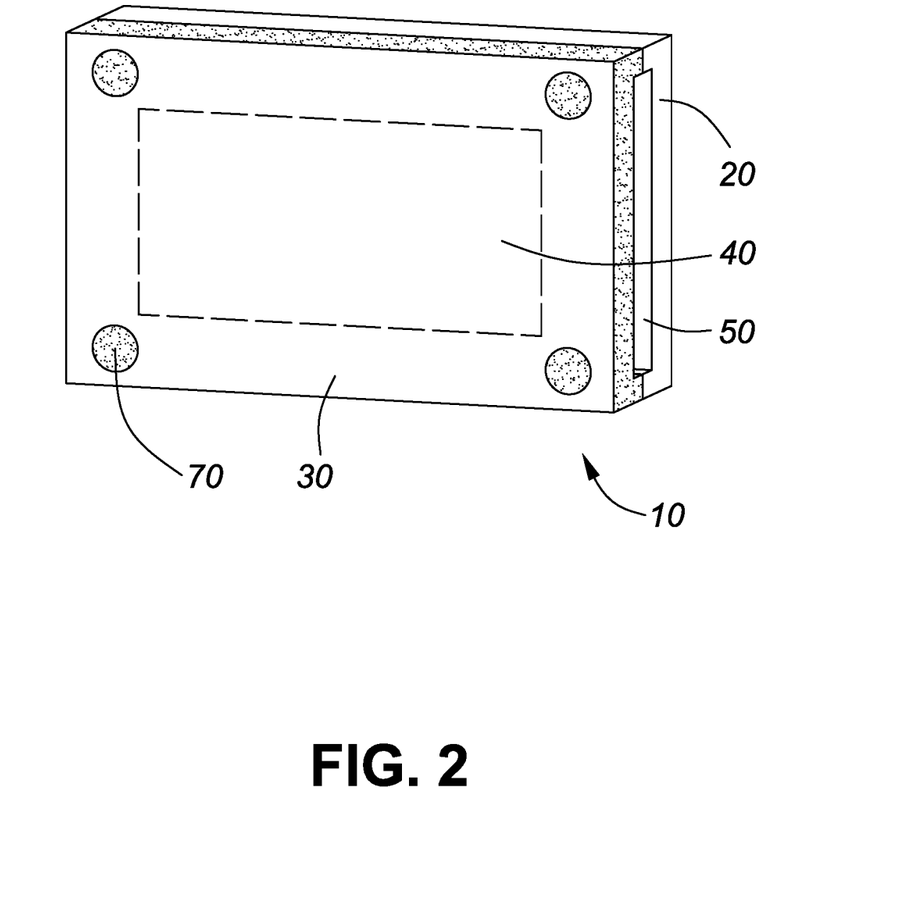
FIG. 2 shows a side view of the sleeve of the device in accordance with an embodiment of the present invention. The sleeve comprises a first porous gas-permeable surface 20, a second surface 30, a pocket or sleeve opening 50, a flatus detector 40 (outlined in a dashed line) inserted within the sleeve, and in a non-limiting example a fastener or attachment device 70 that can be used to attach the sleeve to a garment as described herein.

With reference to FIGS. 1A and 1B, the present disclosure provides a device for detecting a passing of flatus by a patient. The device comprises a sleeve 10, comprising a first porous gas-permeable surface 20 and a second surface 30 attached to the first porous gas-permeable surface 20 to define a pocket 50 within the sleeve 10. A flatus detector 40 may be inserted within the pocket 50 of the sleeve 10 and positioned between the first porous gas-permeable surface 20 and the second surface 30.

In a non-limiting example, the flatus detector may be a colour non-reversible dry-surface carbon dioxide detector (a "non-reversible detector"). The non-reversible detector may be used to detect carbon dioxide gas during the passing of flatus from a patient or subject. However, it is to be understood that the flatus detector may include one or more than one chemical reagents or sensors to determine other gasses that may be present in flatus, for example, but not limited to carbon dioxide, hydrogen, methane, volatile sulfur compounds (such as hydrogen sulfide, methyl mercaptan, methanethiol, dimethyl sulfide, dimethyl disulfide, dimethyl trisulfide), ammonia, indole, skatole, and short chain fatty acids, either alone, or in combination, during the passing of flatus from a patient or subject.

The "non-reversible detector" disclosed herein is intended to detect an incidence of flatus passage (for example but not limited to a "first flatus" of a patient or subject after an abdominal procedure). In the following example, flatus is detected by determining carbon dioxide, however, determination of this gas is provided as an example and is not to be considered limiting as other gasses, as noted above, that are present in flatus may also be determined either alone or in combination. The detector may comprise: (i) an "indicator", for example but not limited to, a dried carbon dioxide indicating solution; and (ii) a carrier substrate onto which the indicator is embedded or applied. The carrier substrate may be flexible or inflexible. Preferably, the carrier substrate is resilient and partially, or semi-flexible.

The indicator, for example, the dried carbon dioxide indicating solution may maintain a first colour in the presence of ambient atmospheric carbon dioxide concentrations and at least a second colour in the presence of increased carbon dioxide concentrations. In the presence of increased carbon dioxide concentrations, the indicator undergoes an irreversible colour change. Specifically, a change from the first colour to at least the second colour of the indicator indicates an increase in carbon dioxide gas concentrations surrounding the non-reversible detector, above ambient atmospheric carbon dioxide concentrations.

Therefore, the indicator may be monitored to determine if there has been a change in the levels of a gas that is greater or less than a baseline level of the gas within the bowel or intestinal tract. The change in the level or amount of gas that is detected may be a rapid change, for example a change taking place within about 1-120 seconds, or any amount therebetween, for example, a change in the level or amount of gas taking place within about 1, 2, 4, 6, 8, 10, 12, 14, 16, 18, 20, 22, 24, 26, 28, 30, 32, 34, 36, 38, 40, 45, 60, 75, 90, 105, 120 seconds or any amount therebetween.

As the non-reversible detector is designed to detect an incidence of flatus passage, the colour of indicator in the non-reversible detector does not revert to the first colour even if, over time, the carbon dioxide concentration in the vicinity around the detector returns to ambient atmospheric carbon dioxide concentrations. In order to avoid "false positive" results, the indicator should have a relatively high humidity resistance, and should not change colour for 1 to 48 hours, or any time therebetween when exposed to ambient atmospheric carbon dioxide concentrations. For example the indicator should not change colour for 1, 2, 3, 4, 5, 6, 7, 8, 9, 10, 12, 14, 16, 18, 20, 22, 24, 26, 28, 30, 32, 34, 36, 38, 40, 42, 46 and 48 hours, or any time therebetween after exposed to ambient atmospheric carbon dioxide concentrations. For example, the indicator should not change colour for at least 5-48 hours, 10-48 hours, 20-48 hours, 30-48 hours, and preferably the indicator does not change colour at all, when exposed to ambient atmospheric carbon dioxide concentrations.

As contemplated in this embodiment, the indicator of the non-reversible detector is a pH-sensitive chemical indicator. The indicator detects an increase in carbon dioxide concentrations when carbon dioxide gas from flatus is present at a concentration that is greater than a pre-determined carbon dioxide concentration threshold, and when the carbon dioxide contacts the indicator. The carbon dioxide chemically reacts with the indicator, alters the pH of the indicator and causes a change in the colour of the indicator. The pre-determined carbon dioxide concentration threshold may be greater than 1, 2, 3, 4, 5, 6, 7, 8, 9, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80%, carbon dioxide, or any amount therebetween. The sensitivity of the indicator to detect a predetermined carbon dioxide concentration, may be calibrated to produce a desired sensitivity, as would be known to one of skill in the art.

Similarly, pH sensitive indicator may detect an increase in one or more other gasses present in flatus that may modify the pH of the pH sensitive indicator in addition to carbon dioxide, for example ammonia gas, hydrogen sulfide, or other component of flatus that may result in a pH change of the pH sensitive indicator. The sensitivity of the indicator to detect a predetermined concentration of the one or more than one gas present in flatus, may be calibrated to produce a desired sensitivity, as would be known to one of skill in the art.

There are various examples in the prior art of colour non-reversible pH-sensitive chemical indicators that may be used for detecting changes in carbon dioxide concentrations, or changes in other gasses present in flatus. As described in U.S. Pat. No. 6,589,761 (which is incorporated herein by reference), colour non-reversible pH-sensitive chemical indicators include Amaranth (red to colorless), Bordeaux (faint pink to yellow/green), Brilliant Ponceaux (orange to colorless), and Napthol Blue Black (green to faint pink). As a non-limiting example, the indicator is preferably Bordeaux.

U.S. Pub. No. 2006/0216828 (which is incorporated herein by reference), describes how dry-surface carbon dioxide detectors can be produced by drying an indicating solution onto a carrier substrate. The indicating solution (i.e. the carbon dioxide detector solution) may comprise one or more of a poly(oxyethylene) based compound, a pH sensitive indicator dye, a suitable organic solvent, and an anionic base. In some instances, the indicating solution further comprises a cationic phase transfer agent. The indicating solution may then be embedded or applied onto carrier substrates of, for example, polyethersulfone strips or disks (e.g. 0.45 µm pore size Supor® material) to form solid dry-surface carbon dioxide detectors. Carbon dioxide detection solutions used to make the dry-surface carbon dioxide detectors do not have to be aqueous. Non-aqueous formulations in organic solvents or formulations that incorporate tiny amounts of water may also be used.

The dimensions of the non-reversible detector may vary. For example, the non-reversible detector, and the carrier substrate, may be fashioned as a thin narrow strip running parallel to the patient or subject, a wide longitudinal strip running perpendicular to the patient or subject, or any angle therebetween.

Alternatively, the indicator may be a pH-sensitive chemical indicator, a non-pH-sensitive chemical indicator, a chemiresistor, or other suitable indicator, for example an NFC tag, as described below.

According to another embodiment of the flatus detector, the flatus detector comprises a gas sensor, such as a chemiresistor. A chemiresistor is a material that changes its electrical resistance in response to changes in the nearby chemical environment. A microprocessor detects a change in the electrical resistance of the chemiresistor, and a transmitter alerts a medical professional if flatus has passed (e.g. by sending a signal to a remote receiver, or illuminating a light affixed to the patient or subject). An example of a chemiresistor gas sensor is described in U.S. Pat. No. 7,737,322, which is incorporated herein by reference in its entirety. The chemiresistor may be incorporated into a garment worn by a patient or subject, such that the chemiresistor overlies a carbon dioxide emissions site (e.g. the anus of the patient or subject). The gas sensor is configured to detect one or more than one of the compounds that may be present in flatus, for example, oxygen, nitrogen, carbon dioxide, hydrogen, methane, volatile sulfur compounds, ammonia, indole, skatole, and short chain fatty acids, either alone, or in combination.

According to another embodiment of the flatus detector, the flatus detector comprises a near field communication ("NFC") tag adapted to detect one or more gases (e.g. carbon dioxide gas, hydrogen gas and the like) present in flatus. NFC tags have the advantages of being inexpensive, requiring no wiring and little energy, and being functional at ambient temperatures. Gas (e.g. carbon dioxide) emissions resulting from flatus can be detected by NFC tags and read by a portable handheld electronic device (e.g. smartphone) or any electronic device that has NFC capability. As described in U.S. Pub. No. 2015/0116093 (which is incorporated herein by reference), commercial NFC tags comprising chemi-responsive nano-materials integrated into their circuitry may be used for portable and inexpensive detection and discrimination of gas phase chemicals. The NFC tag may be used to detect carbon dioxide gas during the passing of flatus from a patient or subject.

An NFC tag may be used to detect one or more gases and may detect one or more successive flatus events, and therefore may transmit information regarding the frequency and intensity of flatus passed by a patient or subject. Such information allows a medical professional to determine the number of episodes of flatus that had occurred in a given time period, for example from 1-48 hours, or any time therebetween, for example 1, 2, 3, 4, 5, 6, 7, 8, 9, 10, 12, 14, 16, 18, 20, 22, 24, 26, 28, 30, 32, 34, 36, 38 40, 42, 44, 46 or 48 hours (or more), or any time therebetween. Multiple passages of flatus would provide greater evidence to a clinician that intestinal motility has improved or has been restored.

Incorporation of Flatus Detector Into a Device

The flatus detector may be incorporated into a device such as a garment that is wearable by a patient or subject, or a capsule that is inserted into or ingested by a patient or subject.

With reference to the FIGS. 1A, 1B, 2, 3A and 3B, the flatus detector, for example, a non-reversible detector, a chemiresistor or an NFC tag, is incorporated into a sleeve 10. The sleeve comprises a first (front) surface 20 made of a porous, gas permeable, material, a second (back) surface 30, and a pocket therebetween 50 for receiving the flatus detector 40. The flatus detector may or may not be sealed within the sleeve 10. The sleeve 10 may further comprise a removable, gas-impermeable covering 60 positioned over the outer surface of the first (porous) surface 20 so that if the flatus detector 40 is inserted within the sleeve 10 prior to use with a patient, exposure of the flatus detector 40 to non-target sources of gas emissions (for example, atmospheric carbon dioxide, or carbon dioxide from health care workers etc.) is reduced. The gas-impermeable covering 60 may be applied to the first surface 20 using an appropriate adhesive that permits the gas-impervious covering to be removed from the first surface prior to use.

The sleeve 10 may come in various sizes. For example which is not to be considered limiting, the patch may come in three sizes, with size 1 for an infant; size 2 for child or teenager; and size 3 for an adult, however other sizes may also be used as required. The different sizes of the flatus detector help accommodate different sizes of patients.

In practice, it is contemplated that the sleeve 10 is positioned on the patient such that the porous (gas permeable) surface lies between the flatus detector 40 and a target gas emission site (e.g. the anus of the patient). For example, the first porous gas-permeable surface 20 of the sleeve 10 may comprise an adhesive over at least a portion, or all, of the surface, the adhesive for attaching the sleeve to a patient so that the flatus detector is positioned near or adjacent the target gas emission site. The adhesive would decrease the likelihood of the flatus detector shifting or moving away from the anus. The adhesive would also assist in containing emitted gas (e.g. flatus) for longer periods of time in the vicinity of the flatus detector. Adhesive on the end of the sleeve closest to the genitalia would be minimized so that hair in the region would not adhere to the adhesive thereby causing discomfort.

Alternatively, the patient or subject may wear a garment such as a diaper for collecting any bodily liquids or solid waste, and the sleeve comprising the flatus detector is positioned near or adjacent the gas emission site. For example, the sleeve 10 comprising the flatus detector 40 may further include a fastener 70 (see FIG. 2) for example, but not limited to, a clip, a snap, a pin, a magnet, a loop and hook fastener, a zipper, an adhesive, or other fastening device, to attach the sleeve 10 comprising the flatus detector 40 to the inside of the garment or diaper. The sleeve 10 comprising the flatus detector 40 may also be stitched, sewn, sealed or permanently attached to the garment or diaper. If the patient has a bowel movement, then intestinal motility has returned and the sleeve incorporating the flatus detector is no longer needed and can be discarded. Advantageously, if the patient has only urinated, then only the diaper may be replaced, thereby leaving the sleeve with the flatus detector in place.

Figure 3A:
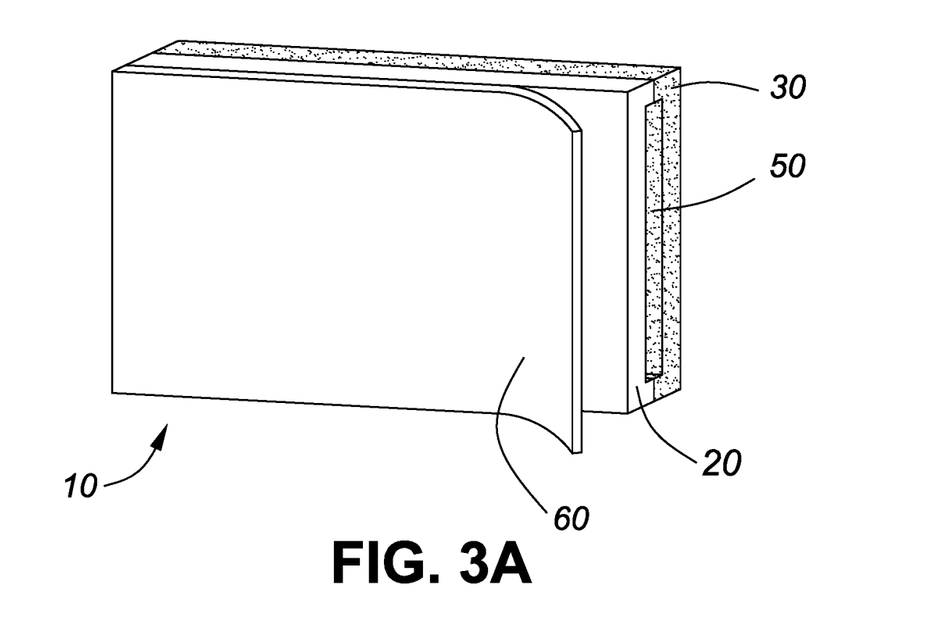
FIG. 3A shows a side view of the sleeve with a first porous gas-permeable surface 20, a second surface 30, a gas-impermeable covering 60, a pocket or sleeve opening 50, for receiving a flatus detector inserted within the sleeve.
Figure 3B:
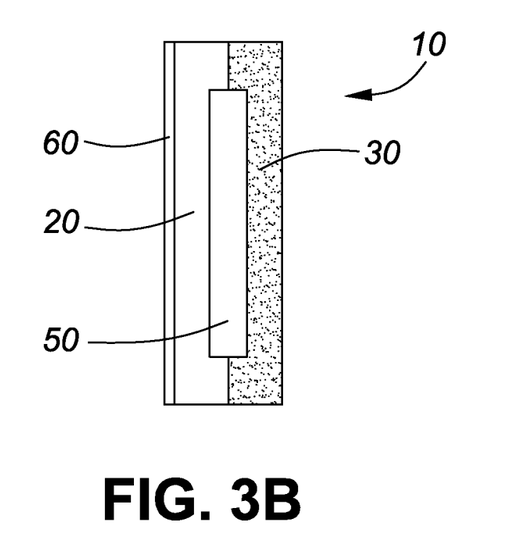
FIG. 3B shows a front end view of the sleeve with the first porous gas-permeable surface 20, the second surface 30, the gas-impermeable layer 60, and the pocket or sleeve opening 50.
Figure 3C:
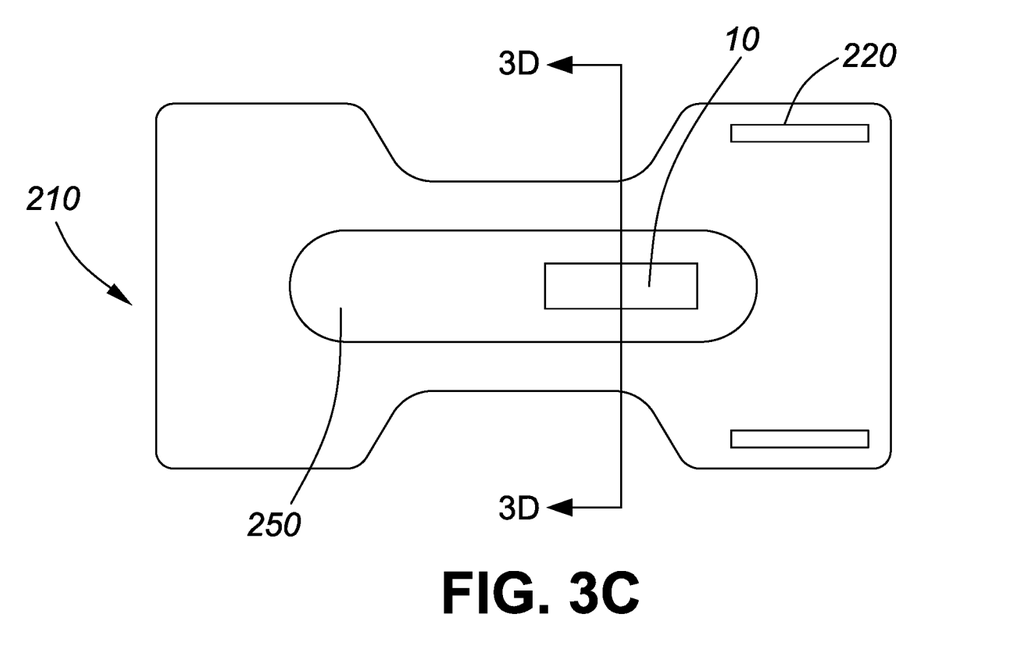
FIG. 3C shows a top plan view of a diaper 210 with a sleeve 10 according to an embodiment of the present invention.
Figure 3D:
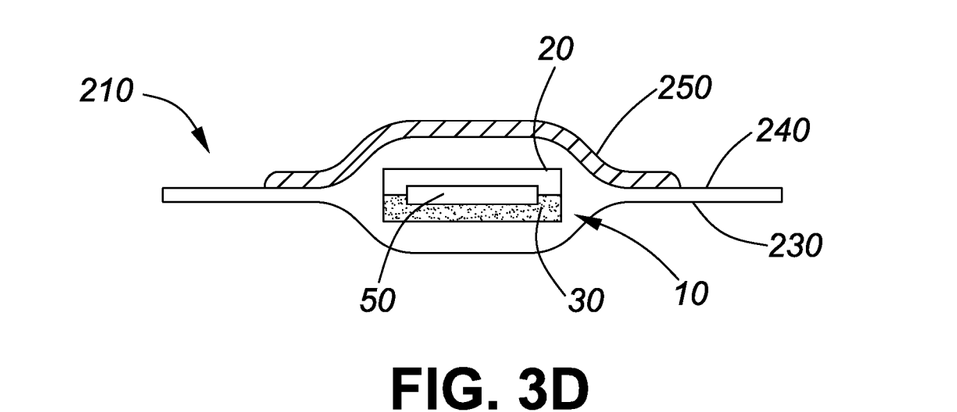
FIG. 3D shows a cross section of the diaper of FIG. 3C.

In another embodiment, the flatus detector is incorporated into a garment, for example, a diaper 210 (FIGS. 3C and 3D). The diaper may be size-adjustable or uni-sized. The diaper comprises fastening components 220 (e.g. adhesive fasteners, cohesive fasteners) that are known in the art. The outer lining 230 of the diaper comprises a material that is generally liquid impermeable. The inner lining 240 of the diaper comprises an absorbent material 250 that is designed to absorb bodily discharge (e.g. urine, sweat, feces, or other bodily fluids). The absorbent material may comprise natural fibers, synthetic fibers, superabsorbent material, or the like, as well as combinations thereof. The inner lining is preferably soft-feeling and non-irritating to the patient's skin.

For example, the sleeve comprising the flatus detector may be incorporated into the diaper 210 so that at least a portion of an inner lining 240 of the diaper acts as the first porous gas-permeable surface (e.g. 20 of FIGS. 1A, 1B), and the second surface (e.g. 30 of FIGS. 1A and 1B) of the sleeve is located between the inner lining 240 and an outer lining 230 of the diaper 210, or the second surface 30 of the sleeve 10 is a portion of the outer lining of the diaper. Furthermore, the sleeve 10 containing the flatus detector 40 may be incorporated between the outer lining 230 and the inner lining 240 of the diaper 210, or on the surface of the inner lining of the diaper that is adjacent the patient's skin.

Alternatively, the diaper 210 may comprise a pocket or sleeve 10 on the inside of the diaper, on the surface of the inner lining 240 adjacent to the patient skin, the pocket for receiving the flatus detector 40. The pocket or sleeve comprising a first (front) surface made of a porous, gas permeable, material, a second (back) surface, and an opening therebetween for receiving the flatus detector. Alternatively, the sleeve may be fashioned by attaching the first porous surface to the inner lining of the diaper to form a sleeve that receives the flatus detector. The flatus detector may, or may not, be sealed within the sleeve. The sleeve may further comprise a removable, gas-impermeable covering (e.g. 60 of FIGS. 3A, 3B) positioned over the outer surface of first (porous) surface so that if the flatus detector is inserted within the sleeve prior to use with a patient, exposure of the flatus detector to non-target sources of emitted gas (for example, from the atmosphere, or health care workers etc.) is reduced. The gas-impermeable covering may be applied to the first surface using an appropriate adhesive that permits the gas-impervious covering to be removed from the first surface prior to use. Alternatively, the sleeve may be packaged in an air-impermeable package so as to minimize the chance of contamination prior to use.

The flatus detector may be positioned in the garment such that at least a portion of the flatus detector overlies a target gas emission source (e.g. the anus of the patient or subject). Preferably, the flatus detector considerably overlies the target gas emission source and surrounding areas such that at least a portion of the non-reversible detector continues to overlie the target gas emission source even if the garment shifts relative to the target gas emission source. The flatus detector is separated from the patient or subject by a porous, gas permeable, barrier, for example, a soft hypoallergenic mesh (the first surface). The porous barrier allows emitted gas to filter through and contact the flatus detector. In embodiments wherein the flatus detector is incorporated between the outer lining and the inner lining of the diaper, then at least a portion of the inner lining of the diaper may act as the porous barrier (first surface). In this embodiment, the inner lining, or the portion of the inner lining that is adjacent the flatus detector, may need to be modified to be made of a porous material in order to provide a porous surface. The sleeve may comprise an opening to receive the flatus detector prior to use of the garment. Alternatively, the flatus detector may be fixed within the sleeve as part of the garment prior to use. The opening of the sleeve may be placed along the inner lining of the garment. Alternatively, the opening of the sleeve may be placed along the outer surface of the garment so that the sleeve and flatus detector may be accessed from the outside of the garment. If the opening of the sleeve is positioned on the outside of the garment, then the sleeve opening should be sealed after the flatus detector is inserted within the sleeve to reduce any leakage of gas from the patient during use. The sleeve may be sealed using any appropriate method as would be evident to one of skill in the art, for example, by adhesive, heat sealing, a gas tight zipper seal and the like.

In embodiments wherein the flatus detector is inserted into a pocket or sleeve inside of the diaper, at least a portion of the porous barrier or first porous gas-permeable surface (e.g. 20 of FIGS. 1A, 1B) of the pocket is adjacent to the patient, when the diaper is fitted to the patient. To minimize dilution of the flatus, the air space between the gas emission source and the flatus detector may be minimized, for example, using a well or tight fitting diaper. To improve containment of flatus for longer periods of time in close proximity to the flatus detector, the garment may be coupled to the patient, for example, using a hypoallergenic adhesive, or elastic ties around the waist and legs. However, the garment may not need to be coupled to the patient if the garment is well fitted.

A diaper may be an advantageous garment in that it cannot be readily removed by a demented or delirious patient, or a young child. As such, the flatus detector incorporated within the diaper would also not be readily removed. To minimize potential contamination of the flatus detector from a patient's urine, the diaper may comprise an additional super absorbent pad to collect and absorb urine and to prevent seepage of urine onto the flatus detector. In addition, the diaper may further comprise a thin inner plastic layer (e.g. polyethylene as described in U.S. Pat. No. 6,589,761) that is permeable to gas (e.g. carbon dioxide gas and hydrogen gas), disposed between the target gas emission source and the flatus detector (e.g. overlaying the porous barrier), the thin inner plastic layer adapted to further minimize any contamination from urine; and any irritation experienced by the patient or subject as a result of the flatus detector. The thin inner plastic layer is permeable to gas (e.g. carbon dioxide gas and hydrogen gas), but impermeable to liquid (e.g. urine).

It is contemplated that at least three different sizes of pads, and at least eight different sizes of diapers may be required to fit individuals of different ages (body habits) from an infant to a morbidly obese adult. However, sizes of the pads and diapers are not limited to at least three or at least eight respectively.

The garment may further comprise a transparent window positioned at back of the garment, on the outward facing surface of the garment that is distal to the emission source, and opposite the porous surface of the inner layer of the garment. In this example, the transparent window may form a portion of the second surface (e.g. 30, of FIGS. 1A and 1B) of the sleeve. The transparent window is positioned in alignment with the flatus detector when the detector is inserted within the sleeve. The transparent window replaces a portion of the back surface of the garment and is affixed to, and sealed with, the back surface of the garment. The sleeve may comprise an opening to receive the flatus detector prior to use of the garment. Alternatively, the flatus detector may be fixed within the sleeve as part of the garment prior to use. The opening of the sleeve may be placed along the inner lining of the garment. Alternatively, the opening of the sleeve may be placed along the outer surface of the garment so that the sleeve and flatus detector may be accessed from the outside of the garment. If the opening of the sleeve is positioned on the outside of the garment, then the sleeve opening should be sealed after the flatus detector is inserted within the sleeve to reduce any leakage of gas from the patient during use. The sleeve may be sealed using any appropriate method as would be evident to one of skill in the art, for example, by adhesive, heat sealing, a gas tight zipper seal and the like. The sleeve may further comprise a removable, gas-impervious covering positioned over the outer surface of first (porous) surface so that if the flatus detector is inserted within the sleeve prior to use with a patient, exposure of the flatus detector to non-target sources of gas emissions (for example, carbon dioxide from the atmosphere, or health care workers etc.) is reduced. The gas-impervious covering may be applied to the first surface using an appropriate adhesive that permits the gas-impervious covering to be removed from the first surface prior to use. Alternatively, the garment may be packaged in an air-impermeable package so as to minimize the chance of contamination of the flatus detector prior to use.

Therefore, in the device as described above, the sleeve may comprise a second surface that may be a portion of the outer lining of the diaper, and the second surface may comprise a transparent window. The flatus detector may be placed between the transparent window of the second surface and at least a portion of the inner lining of the diaper that is the first porous gas-permeable surface prior to use. With this configuration, when the flatus detector is inserted into the sleeve, the flatus detector is then visible through the transparent window. Alternatively, the flatus detector may be inserted between the transparent window of the second surface and at least the portion of the inner lining of the diaper that is the first porous gas-permeable surface, and the sleeve sealed as described above. The flatus detector is inserted within the sleeve so that the carbon dioxide (or other target gas) detector is visible through the transparent window.

The transparent window may be manufactured of a material that is flexible, sturdy, and clear (e.g. a clear plastic film; polyethylene terephthalate plastic as described in U.S. Pat. No. 6,589,761 and incorporated herein by reference). Using such a window, a clinician is able to visually monitor the flatus detector for any signs of flatus passage, without having to remove the garment from the patient or subject. The transparent window is preferably gas-impervious so as to minimize the possibility of contamination of the flatus detector by other gas emitting sources in the vicinity of the patient or subject (e.g. exhaled air of health care workers). In embodiments wherein the garment is a diaper, the transparent window may be incorporated into the outer lining and back of the diaper.

The garment may also comprise a strip of water resistant and tear resistant paper or plastic disposed thereon (e.g. on the front, back, side, bottom, outside, inside etc. . . . ), for allowing a clinician or other healthcare professional to mark when the garment was applied onto the patient or subject. For example, the strip of water and tear resistant paper or plastic comprises a series of columns comprising the numbers from 1 to 31 (31 choices) to represent the days of the month, and the hours from 0000 to 2300 (24 choices) to represent the hours, thereby allowing a healthcare professional to indicate on the garment the day of the month, and the hour of the day, on which the garment was applied onto the patient or subject. A healthcare professional later reading the flatus detector would know whether or not the patient had passed flatus since the date and time the garment comprising the flatus detector was applied.

The sleeve may be affixed to the garment in a tamper-evident manner, so that the garment, sleeve, or both the garment and sleeve, is damageable upon removal of the sleeve from the garment. In an example, the sleeve holding the detector may be coupled to the garment or a patient's body by an adhesive. Upon removal of the sleeve, or garment, the sleeve or a portion of the sleeve remains affixed to the surface to which the adhesive was applied. The act of removing the garment forces the sleeve to irreversibly detach from the garment, thereby damaging the sleeve, garment, or both and indicating to a health care provider that the sleeve or garment has been tampered with. The tamper-evident feature would therefore alert a medical professional to any unexpected tampering of the garment.

In practice, and with respect to minimizing the possibility of false-positive readings owing to the indicator's inadvertent contact with target gases emitted from non-target gaseous sources (e.g. prolonged exposure to atmospheric carbon dioxide concentrations; expired air from clinicians or technicians; etc), a clinician may change the garment (in which the flatus detector is incorporated) every 24-72 hours or even more frequently. Particularly for garments incorporating non-reversible detectors, medical personnel are trained to immediately apply the garment onto the patient after the garment has been removed from the air-impermeable package, or removal of the gas-impervious covering of the porous surface, so as to minimize the chance of contamination. After the garment has been applied, the medical personnel should observe the colour of the indicator of the non-reversible detector for any colour changes. If the indicator has already begun to change colour, or has already changed colour, then the garment should be discarded and a new one applied onto the patient.

Figure 4A:
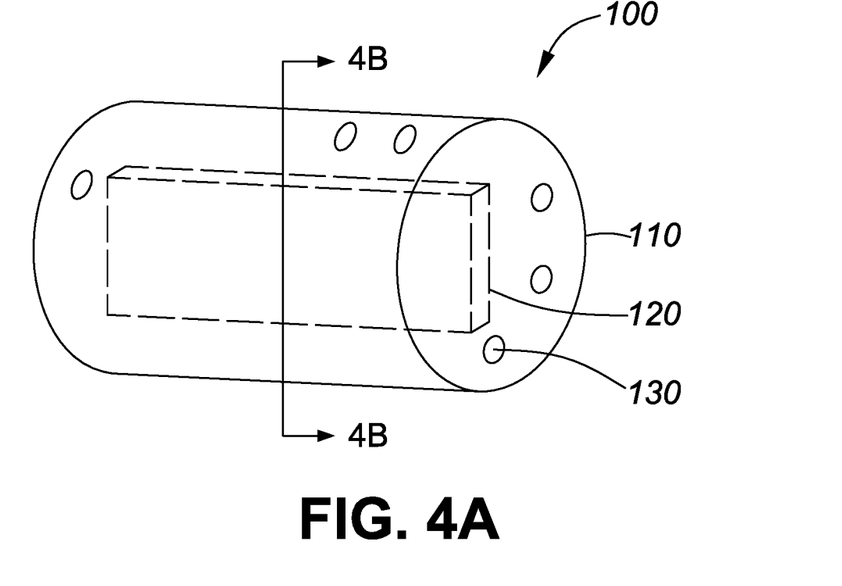
FIG. 4A shows a side view of a flatus detector comprising a capsule 100 housing a detector 120. The shell 110 of the capsule may be perforated 130.
Figure 4B:
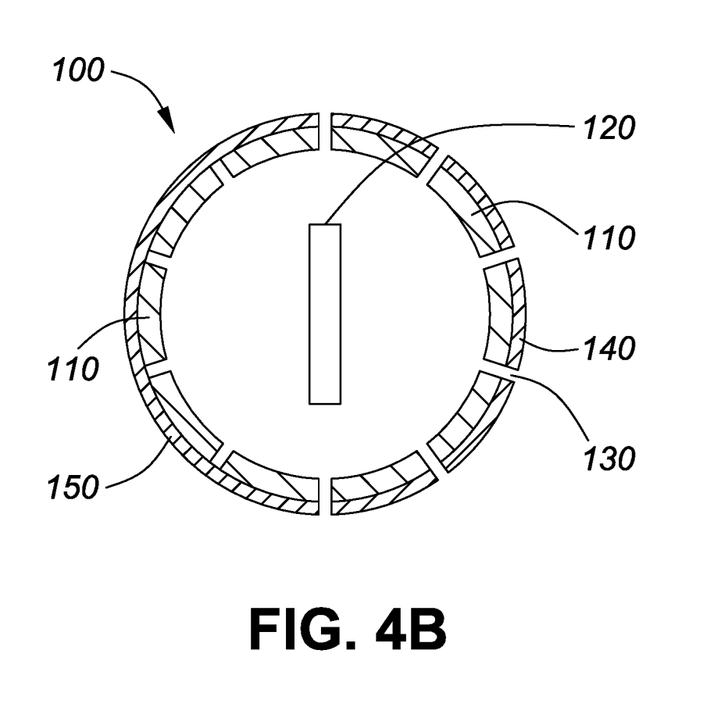
FIG. 4B shows a cross sectional view of the flatus detector of FIG. 4A, and shows two variants for the coating of the capsule. The right hand side of FIG. 4B shows a shell 110 of capsule 100 with perforations 130 that pass through the shell 110 and the coating 130. The left hand side of FIG. 4B shows a shell 110 comprising perforations 130 that pass through the shell 110, but the perforations do not pass through the coating 150. Coating 150 is permeable to one of target gasses and provides a continuous layer over the capsule 100.

With reference to FIGS. 4A and 4B, there is shown an alternative embodiment, and particularly relevant to (though not exclusive to) NFC tag flatus detectors. The flatus detector comprises a capsule 100 with a shell 110. The capsule can be a small, cylindrical-shaped device (or other shape) that passes naturally through the body without discomfort. The shell 110 comprises a plurality of small perforations 130 to allow one or more target gas to penetrate the shell 110, and interact with the enclosed flatus detector 120, for example, an NFC tag, chemiresistor, or other similar detector. The inside, middle, or outside of the capsule may be lined with a thin plastic layer, preferably a biocompatible layer, for example, a polyethylene as described in U.S. Pat.

No. 6,589,761 (which is incorporated herein by reference), the thin plastic layer being permeable to at least carbon dioxide gas but impermeable to solids or liquids. In some embodiments, the capsule further comprises a super-hydrophobic coating, for example, a nanoscopic surface layer, such as a manganese oxide polystyrene or a silica nanocoating, to further repel organic waste and liquids away from the capsule. In the example shown in FIG. 4B, the shell 110 of capsule 100 is coated with a coating 140 with perforations (shown on the right hand side of capsule) or a continuous coating 150 (shown on the left hand side of capsule). The coating may be discontinuous as shown in 140 so that the coating is also perforated in a manner similar to the shell 110 of capsule 100, and permits one or more target gas to enter the capsule 100 and interact with detector 120. Alternatively, the coating may be continuous 150, and permeable to the one or more target gas, so that one or more target gas may permeate the coating 150, and enter the capsule 100 via perforations 130, and interact with the detector 120. The coating 140 or 150 may be a polyethylene coating, a hydrophobic coating or other biocompatible coating.

An example of a capsule that may be used as described herein is a PillCam® capsule, which measures 11 mm×32 mm, weighs less than 4 grams, and passes naturally through the body without discomfort. The PillCam® capsule however, may need to be modified to permit gas entry as required by the methods of the present invention.

The chemiresistor, NFC tag, or similar detector is configured to detect one or more target gasses that may be present within the bowel or intestinal tract, in a patient or subject. The target gas may be, but is not limited to carbon dioxide, hydrogen, methane, volatile sulfur compounds (such as hydrogen sulfide, methyl mercaptan, methanethiol, dimethyl sulfide, dimethyl disulfide, dimethyl trisulfide), ammonia, indole, skatole, and short chain fatty acids, either alone, or in combination.

The capsule flatus detector 100 is deposited into the intestinal tract by a medical professional. It is contemplated that the capsule comprising the flatus detector is introduced into the repaired bowel after surgery (e.g. pushed distal to the site of surgery). In the alternative, it is contemplated that the capsule is inserted into the rectum when inserting it more proximally in the bowel is not deemed to be advantageous, safe, or possible. While placing the capsule directly in the bowel or rectum immediately increases the ambient target gas concentrations surrounding the flatus detector, the flatus detector may instead be programmed or modified to detect significant and rapid change in the target gas concentrations that would indicate the movement of flatus through the intestinal tract, thereby alerting a clinician that intestinal peristalsis is returning. Particular to chemiresistors and NFC tags, an optimal number of fluctuations in target gas concentration (e.g. carbon dioxide gas, or other target gas, concentrations) may serve as an indication of the return of intestinal peristalsis (i.e. intestinal motility). Such pre-programmed factors may be incorporated into the recording software of the chemiresistor, NFC tag, or other similar detector, to assist a clinician to decide whether the number of recorded changes in target gas concentrations was clinically significant.

In practice, and particularly where the capsule is directly inserted into the rectum, it is preferable that the rectum be cleaned (e.g. with an enema) to prevent stool from covering the capsule upon entry into the rectum. Stool in the perforations of the capsule may prevent gas (e.g. carbon dioxide gas, hydrogen gas) from accessing the flatus detector within the capsule. In patients or subjects suffering from a significant bowel obstruction, a clinician may clean the rectum by manually removing, with a gloved finger, any stool in the rectum that may interfere with the function of the flatus detector in the capsule. Advantageously, a super-hydrophobic coating, if applied to the capsule, assists in repelling liquid and stool away from the capsule (and therefore the flatus detector located within the capsule).

Capsules comprising NFC tag flatus detectors advantageously transmit electronic signals regardless of their location in the intestinal system to a processing device, for example a CPU, microprocessor, mobile telephone or mobile device comprising a CPU, the CPU, microprocessor, or mobile device comprising a receiver to receive data from the detector, and one or more algorithm or program to process the data transmitted from the detector. Multiple capsules comprising NFC tag flatus detectors may be inserted at different places within the intestinal tract to detect changes in carbon dioxide concentrations at multiple locations along the intestinal tract, thereby improving the ability to determine whether bowel function has returned to appropriate levels. For example, one capsule could be placed in the bowel after surgery, one could be placed in the rectum, and potentially one could be swallowed. Moreover, patients or subjects would not be able to easily remove the capsule comprising flatus detectors therein from their rectum or intestine.

Therefore the present invention also provides a device for detecting a passing of flatus by a patient comprising, a capsule 100 comprising a perforated shell 110, the shell covered with a discontinuous biocompatible coating comprising perforations 130, or a continuous gas-permeable biocompatible coating 150, and a flatus detector 120 inserted within the shell 110. Also provided is a method of detecting a passing of flatus by a patient comprising, positioning this capsule 100 within a bowel or intestinal tract of the patient, and monitoring the device to determine if the flatus detector indicates levels of a gas that is greater than a baseline level of the gas within the bowel or intestinal tract. The detector may transmit electronic signals to a processing device that receives the data and process the data to determine if there have been changes in the levels of one or mare target gas in the bowel or intestinal tract.

It is contemplated that any part of any aspect or embodiment discussed in this specification can be implemented or combined with any part of any other aspect or embodiment discussed in this specification. While particular embodiments have been described in the foregoing, it is to be understood that other embodiments are possible and are intended to be included herein. It will be clear to any person skilled in the art that modification of and adjustment to the foregoing embodiments, not shown, is possible.

What is claimed is:

1. A device for detecting a passing of flatus by a patient comprising, a sleeve comprising a first porous gas-permeable surface comprising a liquid impermeable layer that is gas-permeable, and a second surface attached to the first porous gas-permeable surface, the first porous gas-permeable surface and the second surface defining a pocket within the sleeve, and a flatus detector inserted within the pocket of the sleeve and positioned between the first porous gas-permeable surface and the second surface, the device configured to be placed on the patient so that the first porous gas permeable surface comprising the liquid impermeable layer is configured to lie between the flatus detector and a target gas emission site of the patient.

2. The device of claim 1, wherein the first porous gas-permeable surface is a hypoallergenic mesh.

3. The device of claim 1, wherein the sleeve further comprises a fastener attached to the sleeve, the fastener for attaching the sleeve to a garment.

4. The device of claim 1, wherein the flatus detector is a dry-surface carbon dioxide detector comprising a carbon dioxide indicating solution that is dried onto, embedded into, or applied onto a carrier substrate, the carbon dioxide indicating solution undergoing an irreversible colour change in a presence of increased carbon dioxide concentrations.

5. The device of claim 4, wherein the dried carbon dioxide indicating solution is pH-sensitive.

6. The device of claim 5, wherein the dried pH-sensitive carbon dioxide indicating solution is selected from Bordeaux, Amaranth, Brilliant Ponceaux, and Napthol Blue Black.

7. The device of claim 1, wherein the flatus detector is a chemiresistor or a near field communication tag.

8. The device of claim 7, wherein chemi-responsive nano-materials are integrated into circuitry of the near field communication tag.

9. The device of claim 1, wherein the device is a garment and the sleeve comprises a fastener attached to the sleeve, and the sleeve is attached to an inner lining of the garment via the fastener, or the sleeve is stitched, sewn, sealed or permanently attached to the garment.

10. The device of claim 9, wherein the garment is a diaper.

11. The device of claim 1, wherein the device is a diaper, and the sleeve comprising the flatus detector is incorporated into the diaper so that at least a portion of an inner lining of the diaper is the first porous gas-permeable surface, and the second surface of the sleeve is located between the inner lining and an outer lining of the diaper, or the second surface of the sleeve is a portion of the outer lining of the diaper that is liquid and gas-impermeable.

12. The device of claim 11, wherein the second surface is a portion of the outer lining, and the second surface comprises a transparent window, the flatus detector for placement between the transparent window of the second surface and at least the portion of the inner lining of the diaper that is the first porous gas-permeable surface, so that when the flatus detector is inserted into the sleeve, the flatus detector is visible through the transparent window.

13. The device of claim 11, wherein the second surface is a portion of the outer lining, and the second surface further comprises a transparent window, the flatus detector inserted between the transparent window of the second surface and at least the portion of the inner lining of the diaper that is the first porous gas-permeable surface, so that the flatus detector is visible through the transparent window.

14. The device of claim 12, wherein the portion of the inner lining of the diaper that is the first porous gas-permeable surface is further coupled to a gas-permeable hydrophobic layer.

15. The device of claim 1 wherein the first porous gas-permeable surface comprises an adhesive over a portion of the surface, the adhesive for attaching the sleeve to the patient.

16. The device of claim 1 wherein the second surface is gas permeable or comprises a gas-permeable hydrophobic layer.

17. The device of claim 11 wherein the second surface is gas permeable or comprises a gas-permeable hydrophobic layer.

18. The device of claim 1, wherein the flatus detector includes one or more than one chemical reagents or sensors to determine, carbon dioxide, hydrogen, methane, hydrogen sulfide, methyl mercaptan, methanethiol, dimethyl sulfide, dimethyl disulfide, dimethyl trisulfide, ammonia, indole, skatole, and a combination thereof.

19. A method of detecting a passing of flatus by a patient comprising:

(a) positioning the device of claim 1 over at least a portion of an anus of the patient, such that the flatus detector covers at least the portion of the anus of the patient: and (b) monitoring, by the flatus detector, a level of a gas that is greater than atmospheric levels of the gas indicates that the patient has passed flatus.

20. The method of claim 17, wherein in the step of positioning (step a), the sleeve is attached to a garment, and positioned so that at least a portion of the flatus detector is configured to overlie at least the portion of the anus of the patient.

21. The method of claim 20, wherein the garment is a diaper.

22. The method of claim 21, wherein the sleeve comprising the flatus detector is incorporated into the diaper so that at least a portion of an inner lining of the diaper is the first porous gas-permeable surface, and the second surface of the sleeve is located between the inner lining and an outer lining of the diaper, or the second surface of the sleeve is a portion of the outer lining of the diaper that is liquid and gas-impermeable.

23. A garment for detecting flatus comprising, a sleeve comprising a first porous gas-permeable surface comprising a liquid impermeable, layer that is gas-permeable, and a second surface attached to the first porous gas-permeable surface, the first porous gas-permeable surface and the second surface defining a pocket within the sleeve, and a flatus detector inserted within the pocket of the sleeve, between the first porous gas-permeable surface and the second surface, the sleeve positioned within the garment so that when the garment is fitted to a patient, the first porous gas permeable surface comprising the liquid impermeable layer is configured to lie between the detector and a target gas emission site of the patient, and at least a portion of the flatus detector is configured to overlie an anus of the patient.

24. The garment of claim 23, wherein at least a portion of an inner lining of the garment is the first porous gas-permeable surface, and the second surface of the sleeve is located between the inner lining and an outer lining of the garment, or the second surface of the sleeve is a portion of the outer lining of the garment.

25. The garment of claim 24, wherein the garment is a diaper.

26. An assembly for detecting a passing of flatus by a patient, the assembly comprising, a garment, and the device of claim 1 coupled to the garment.

27. The assembly of claim 26, wherein the sleeve of the device comprises a fastener attached to the sleeve, and the sleeve is attached to an inner lining of the garment via the fastener, or the sleeve is stitched, sewn, sealed, or permanently attached to the garment.

28. The assembly of claim 26, wherein the garment is a diaper.

* * * * *